United States Patent
Hofer (10) Patent No.: US 10,305,293 B2
(45) Date of Patent: May 28, 2019

(54) BATTERY MANAGEMENT SYSTEM

(71) Applicant: Infineon Technologies AG, Neubiberg (DE)

(72) Inventor: Guenter Hofer, St. Oswald (AT)

(73) Assignee: Infineon Technologies AG, Neubiberg (DE)

( * ) Notice: Subject to any disclaimer, the term of this patent is extended or adjusted under 35 U.S.C. 154(b) by 275 days.

(21) Appl. No.: 14/286,241

(22) Filed: May 23, 2014

(65) Prior Publication Data

US 2015/0340888 A1    Nov. 26, 2015

(51) Int. Cl.
| | |
|---|---|
| *H02J 7/00* | (2006.01) |
| *G01K 13/00* | (2006.01) |
| *G01N 7/00* | (2006.01) |
| *G01N 21/25* | (2006.01) |
| *G01R 31/382* | (2019.01) |
| *G01R 31/389* | (2019.01) |
| *H01M 10/48* | (2006.01) |
| *H04Q 9/00* | (2006.01) |
| *H01M 10/42* | (2006.01) |

(52) U.S. Cl.
CPC ............ *H02J 7/0021* (2013.01); *G01K 13/00* (2013.01); *G01N 7/00* (2013.01); *G01N 21/25* (2013.01); *G01R 31/382* (2019.01); *G01R 31/389* (2019.01); *H01M 10/425* (2013.01); *H01M 10/48* (2013.01); *H01M 10/486* (2013.01); *H04Q 9/00* (2013.01); *H01M 2010/4271* (2013.01); *H01M 2010/4278* (2013.01)

(58) Field of Classification Search
CPC ...................................................... H02J 7/0021
See application file for complete search history.

(56) References Cited

U.S. PATENT DOCUMENTS

| | | | |
|---|---|---|---|
| 6,184,656 B1 * | 2/2001 | Karunasiri ............ | B60L 3/0046 180/65.8 |
| 6,469,635 B1 * | 10/2002 | Hudson ................. | E21B 47/122 175/40 |
| 9,209,477 B2 | 12/2015 | Al-Kadi et al. | |
| 9,608,300 B2 | 3/2017 | Washiro | |
| 2007/0001651 A1 * | 1/2007 | Harvey ................. | H02J 7/0016 320/166 |

(Continued)

FOREIGN PATENT DOCUMENTS

| | | |
|---|---|---|
| CN | 103210561 A | 7/2013 |
| CN | 103580091 A | 2/2014 |
| JP | WO 2014147896 A1 * | 9/2014 ............ H02J 7/0021 |

OTHER PUBLICATIONS

Washiro, WO2014147896 translation Management Device, Communication Device, Management Method, and Management Sep. 2014.*

(Continued)

*Primary Examiner* — Robert J Grant
*Assistant Examiner* — Tynese V McDaniel
(74) *Attorney, Agent, or Firm* — Shumaker & Sieffert, P.A.

(57) ABSTRACT

A device comprises a control entity configured to monitor an operation parameter of at least one battery cell of a battery. The device further comprises an interface coupled with a power line of the battery and configured to transceive control data via at least one of load modulation or load demodulation of a power line signal of the power line.

21 Claims, 11 Drawing Sheets

(56) References Cited

U.S. PATENT DOCUMENTS

| | | | |
|---|---|---|---|
| 2011/0202213 A1* | 8/2011 | Rosendahl | B60L 11/1816 701/22 |
| 2013/0002208 A1* | 1/2013 | Rozenboim | H02J 7/0021 320/162 |
| 2013/0234839 A1* | 9/2013 | Williams | G08C 19/04 340/12.32 |
| 2013/0285616 A1* | 10/2013 | Washiro | H01M 10/44 320/134 |
| 2014/0028249 A1* | 1/2014 | Larsen | H02J 7/022 320/107 |
| 2014/0035357 A1 | 2/2014 | Hausmann et al. | |
| 2014/0042957 A1* | 2/2014 | Al-Kadi | H01M 10/482 320/103 |
| 2014/0097672 A1* | 4/2014 | Takemura | H01M 10/4257 307/9.1 |
| 2015/0311571 A1* | 10/2015 | Krauss | H01M 10/0431 429/61 |

OTHER PUBLICATIONS

Office Action, in the Chinese language, from counterpart Chinese Application No. 201510253413.5, dated Apr. 5, 2017, 7 pp.

\* cited by examiner

BATTERY MANAGEMENT SYSTEM

TECHNICAL FIELD

The present application relates to methods, devices, and systems used to monitor an operation parameter of a battery.

BACKGROUND

In various technological fields, batteries are used as an energy supply. Such technological fields comprise, but are not limited to: automotive applications such as start-up batteries and batteries of electrically powered vehicles, aviation applications, mobile devices, etc.

Each battery may comprise a plurality of battery cells. Further, a plurality of batteries may be electrically connected in series via a power line. A battery stack is formed. By such series connection, a defined voltage may be provided, the voltage amounting to more than ten, more than hundred, two-hundred or five-hundred volts.

Sometimes battery management systems (BMS) are employed. BMSs may comprise one or more devices configured to monitor at least one operation parameter of the battery cells of the batteries. The at least one operation parameter may be indicative of, e.g., a state of charge (SOC) of the battery stack and/or a state of health (SOH) of the battery. A master unit may determine these or corresponding parameters and employ them for battery management. Often, the logic of the BMS resides in the master unit which is configured to control the devices. Control data is exchanged between the master unit and the devices.

In conventional systems, dedicated control signal wiring is provided between the master unit and each device. Sometimes, serial/linear or star-shaped bus systems are employed for the signalling of the control data. This may result in certain drawbacks.

For example, the control signal wiring may require significant space and resources. It may be subject to wear-out and failure. Bus systems may result in spatially dependent heating due to different levels of work load for the various devices, depending on their position in the bus system with respect to the master unit. Further, in particular when employing a serial bus system, the traffic on some parts of the bus system may be comparably high resulting in delays in transmission of the control data. Congestion of the data transmission may result.

DETAILED DESCRIPTION OF ILLUSTRATIVE EMBODIMENTS

In the following, illustrative embodiments will be described with reference to the attached drawings. It is to be noted that these embodiments serve illustrative purposes only and are not to be construed as limiting the scope of the present application. For example, while embodiments may be described as comprising a plurality of elements, in other embodiments some of these elements may be omitted and/or replaced by alternative elements. In still other embodiments, additional elements may be provided. Furthermore, elements from different embodiments may be combined with each other to form additional embodiments unless specifically noted otherwise.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Direct connections or couplings shown in the drawings or described herein, i.e., connections or couplings without intervening elements, may be replaced by indirect connections or couplings, i.e., connections or couplings comprising one or more intervening elements, and vice versa, as long as the general function of the respective connection or coupling, for example, to transmit a certain kind of information, is maintained. While in some embodiments connections or couplings shown in the drawings or described herein may be implemented as wire-based connections or couplings, for example, using conductive paths within an integrated circuit, in other embodiments some or all of such connections or couplings may also be implemented using wireless connections or couplings unless specifically noted otherwise.

In various fields relating to batteries, need exists for advanced techniques of battery management avoiding drawbacks as mentioned above. In particular, a need exists for such techniques of battery management which allow for lean and efficient and fail-safe signalling of control data.

The present application relates to a device comprising a control entity configured to monitor an operation parameter of a battery cell, to a system, and to a corresponding method. Hereinafter techniques of battery management of one or more batteries, each comprising a plurality of battery cells, are described. Typically, a plurality of batteries is electrically connected in series via a power line thereby forming a battery stack. The battery cells of each battery are likewise electrically coupled in series. Instead of dedicated control signal wiring for a communication between monitoring devices and a master unit, the control data is transmitted and/or received, i.e., transceived, via the power line. For this, the control data is modulated onto a power line signal of the power line, i.e., power line signaling is employed. Robust and efficient power line signaling is achieved by load modulation and/or load demodulation.

The techniques can be applied on different hierarchy levels of the BMS architecture. In particular, power line signaling by at least one of load modulation or load demodulation may be employed for communication with satellite monitoring devices associated with a battery cell (battery-cell level) on the one hand side, and/or monitoring devices associated with a battery (battery level) on the other hand side.

According to various embodiments, a device is provided. The device comprises a control entity configured to monitor an operation parameter of at least one battery cell of a battery. The device further comprises an interface coupled with a power line of the battery. The interface is configured to transceive control data via at least one of load modulation or load demodulation of a power line signal of the power line.

According to various embodiments, a system is provided. The system comprises a plurality of batteries electrically connected in series via a power line. The system further comprises a plurality of devices. Each one of the plurality of devices is associated with a respective one of the plurality of batteries. Each device comprises a control entity configured to monitor an operation parameter of at least one battery cell of the associated battery. Each device further comprises an interface coupled with the power line and configured to transceive control data via at least one of load modulation or load demodulation of a power line signal of the power line.

According to various embodiments, a system is provided. The system comprises a plurality of battery cells of a battery. The battery cells are electrically connected in series via a power line. The system further comprises a plurality of devices. Each one of the plurality of devices is associated with a respective one of the plurality of battery cells. Each device comprises a control entity configured to monitor an operation parameter of the associated battery cell. Each device further comprises an interface coupled with the power line. The interface is configured to transceive control data via at least one of load modulation or load demodulation of a power line signal of the power line.

According to further embodiments, other devices, systems, or methods may be provided. Such embodiments will be apparent from the following detailed description in connection with the accompanying drawings.

Figure 1:
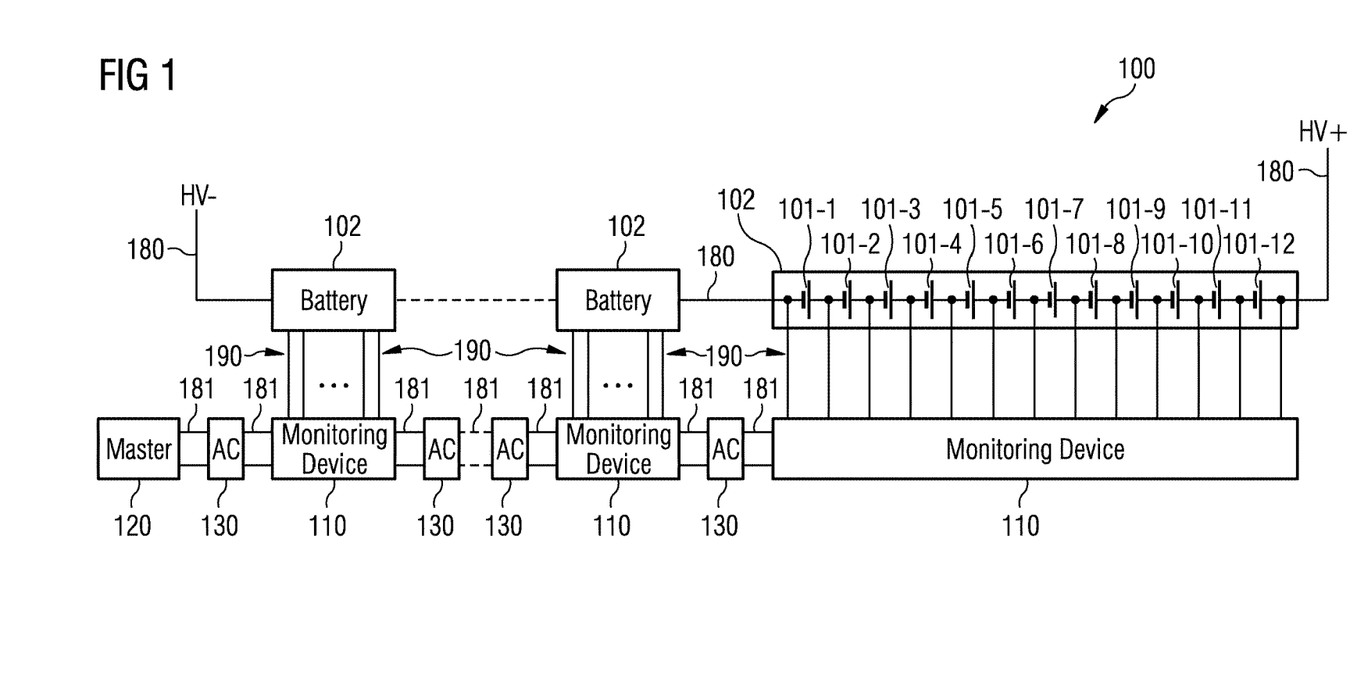
FIG. 1 illustrates a conventional BMS.

In FIG. 1, a conventional BMS 100 is shown. The BMS 100 comprises three batteries 102 which are electrically connected in series via the power line 180. The plurality of batteries 102 is sometimes referred to as a battery stack. Between the input and output of the power line 180, a voltage is provided (labeled in FIG. 1 with HV+ and HV−); this voltage is typically the sum of the open circuit voltages of the plurality of batteries 102. As a result, each one of the batteries is situated on a different voltage level.

As exemplarily shown for one of the batteries, each battery 102 comprises a plurality of battery cells 101-1-101-12 electrically connected in series via the power line 180 within each battery 102. The BMS 100 further comprises a plurality of monitoring devices 110. Each one of the plurality of monitoring devices 110 is associated with a respective one of the plurality of batteries 102. For this, control signal wiring 190 is provided between the monitoring device 110 and the battery 102. E.g., one or more sensors may be arranged within or close to the battery 102; the sensors may be read out and/or controlled via this control signal wiring 190. The monitoring devices 110 are configured to monitor one or more operation parameters of the battery cells 101-1-101-12 of the batteries 102.

Further, a master unit 120 is provided which is configured to control the plurality of monitoring devices 110. For this, control signal wiring 181 is provided. The monitoring devices 110 are connected via a serial bus system formed by the control signal wiring 181 with the master unit 120. Isolators 130 are provided between the various monitoring devices 110 and the master unit 120, respectively. The isolators 130 DC-decouple, respectively AC-couple, the various monitoring devices 110 and the master unit 120, as these entities 110, 120 are typically situated on different voltage levels as explained above.

Typically, the control logic resides in the master unit 120. The monitoring devices 110 may be equipped with comparably less or no logic and respond and report to the master unit 120; this is illustrated in the following example: The master unit 120 transmits packetized control data to each one of the monitoring devices 110 to control the operation; this packetized control data may include a command as payload. In response to the receiving of such control data, each monitoring device 110 is configured to monitor the operation parameter of the associated battery cells 101-1-101-12. Then, the packetized control data may be transmitted from the respective monitoring device 110 to the master unit 120; this control data may include the operation parameter which has been previously determined by the respective monitoring device 110 as payload. Thereby, the master unit 120 may collect the operation parameters of the various battery cells 101-1-101-12 and batteries 102 of the BMS 100 and, from this, calculate a status parameter such as SOC and/or SOH and/or overvoltage and/or undervoltage and/or overtemperature. Thereby, it may be checked whether certain safety requirements are met, i.e., whether the battery is operated in a safe state.

The BMS 100 of FIG. 1 has certain drawbacks. For example, the traffic of control data of those monitoring devices 110 which are situated closer to the master unit 120 may exceed the traffic of those monitoring devices 110 which are located more remote from the master unit 120. A power consumption, respectively heating of the monitoring devices 110 may be proportional to the traffic; thereby, spatially dependent heating of the monitoring devices 110 may occur in the BMS 100. This may result in spatially dependent wear out of the monitoring devices 110. This may reduce the reliability and increase maintenance costs. Further, the increased power consumption of certain monitoring devices 110 typically results in a faster discharge of the associated battery 102; namely, the associated battery 102 is often used to power the associated monitoring device 110. Then, certain batteries 102 may discharge faster or slower than other batteries 102. Further, the control signal wiring 181 may be expensive to manufacture, require space in the BMS 100, and may be subject to failure. Further, the traffic capacity of the control signal wiring 181 may be limited. In particular, a plurality of the monitoring devices 110 may communicate via one and the same line section of the control signal wiring 181. Thereby, control data to be transmitted via the control signal wiring 181 may be delayed due to congestion.

Figure 2:
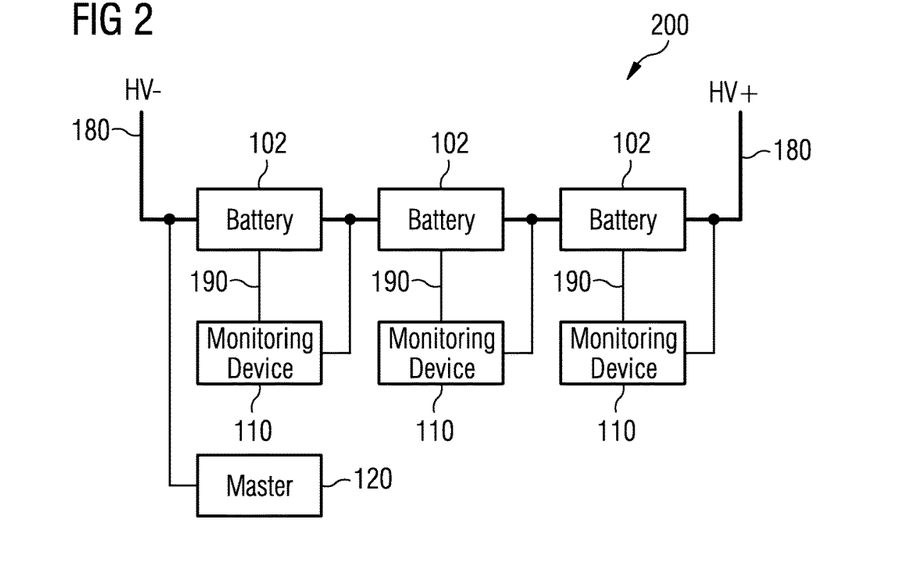
FIG. 2 schematically illustrates a BMS according to various embodiments.

In FIG. 2, a schematic illustration of a BMS 200 according to various embodiments is shown. Here, the dedicated control signal wiring 181 of conventional systems (cf. FIG.

1) is replaced by power line signaling via the power line 180. The control data is modulated onto the power line signal. For this, the master unit 120 is coupled with the power line 180. Further, each one of the monitoring devices 110 may be coupled with the power line 180.

Figure 3:
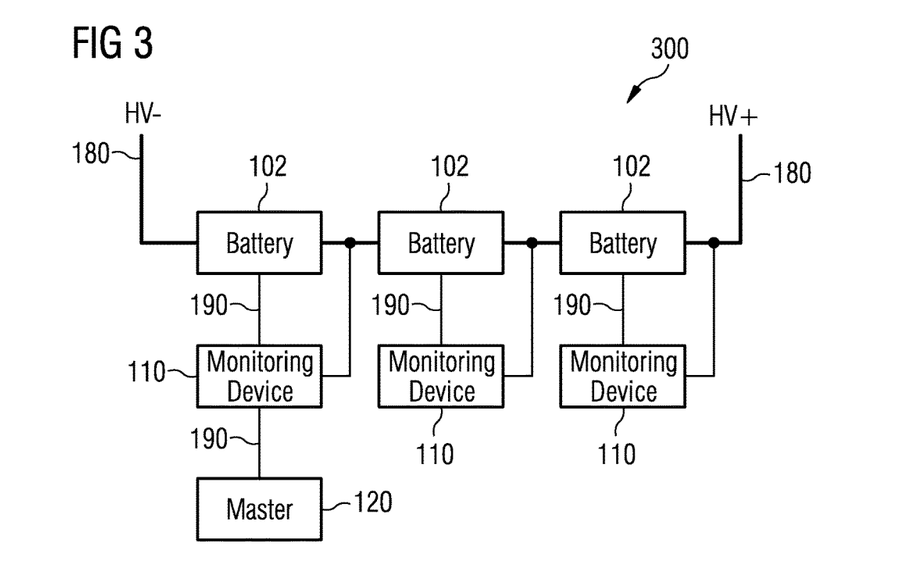
FIG. 3 schematically illustrates a BMS according to various embodiments.

An alternative scenario of a BMS 300 is shown in FIG. 3. Here, the master unit 120 of a BMS 300 is directly coupled via control signal wiring 190 to one of the monitoring devices 110 which may act as a transponder for control data exchanged between the master unit 120 and the remaining monitoring devices 110.

Figure 4:
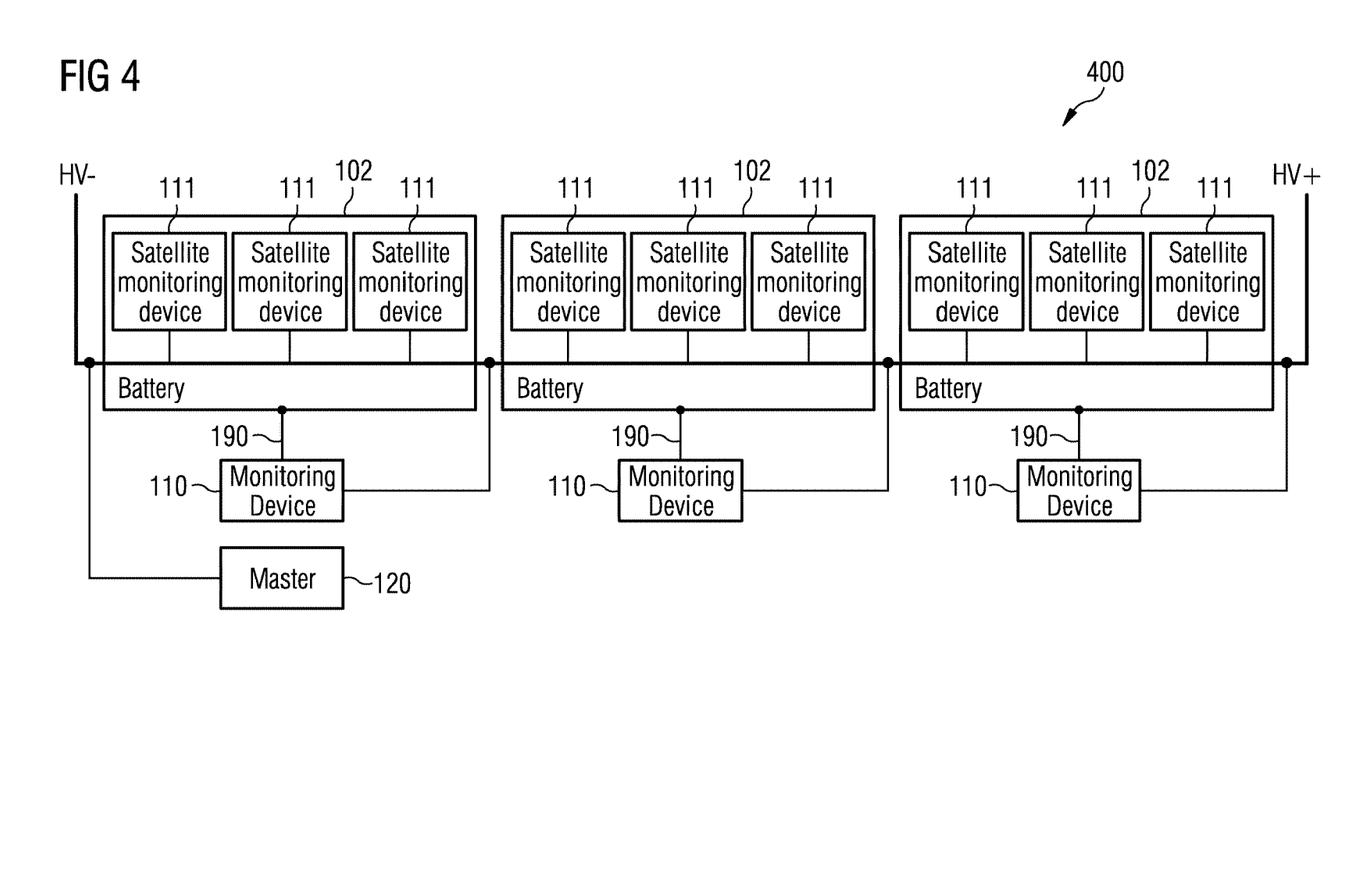
FIG. 4 schematically illustrates a BMS according to various embodiments, the BMS comprising satellite monitoring devices.

In FIG. 4, a BMS 400 comprising the monitoring devices 110, as well as satellite monitoring devices 111 is shown. Each one of the satellite monitoring devices 111 is associated with a respective one of the plurality of battery cells 101-1-101-12 (not shown in FIG. 4). The satellite monitoring devices 111 may be situated within the housing of the respective batteries 102. Some of the tasks conventionally assigned to the monitoring devices 110 may be performed by the satellite monitoring devices 111, e.g., the monitoring of certain operation parameters such as pressure, dilatation, and temperature of the associated battery cell.

In the scenario of FIG. 4, each one of the satellite monitoring devices 111 may be configured to transceive the control data via at least one of load modulation or load demodulation of the power line signal. By such means, each one of the satellite monitoring devices 111 may communicate directly with the master unit 120 and/or with the associated monitoring device 110. In latter case, the monitoring devices 110 may act as transponders and be configured to forward the control data exchanged between the master unit 120 and the satellite monitoring devices 111. In any case, the monitoring devices 110 themselves may be configured to communicate with the master unit 120 via at least one of load modulation or load demodulation of the power line signal.

Figure 5:
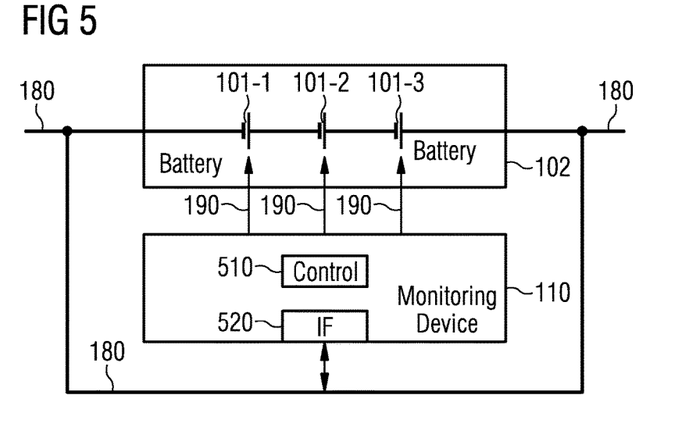
FIG. 5 illustrates a battery and an associated monitoring device according to various embodiments.

A more detailed view of a monitoring device 110 associated with a battery 102 is shown in FIG. 5. The battery 102 comprises three battery cells 101-1, 101-2, 101-3. Of course, it is possible that the battery 102 comprises a larger or smaller number of battery cells 101-1-101-3. Often, a number in the order of 12, 24 or 48 battery cells 101-1-101-3 is employed. Control signal wiring 190 is provided between the monitoring device 110 and the battery 102; in the scenario of FIG. 5, a dedicated control signal wiring 190 for each of the battery cells 101-1-101-3 is provided. Via the control signal wiring 190, a control entity 510 of the monitoring device 110 is configured to monitor the respective operation parameter of the three battery cells 101-1-101-3. For this purpose, a sensor device or the like may be provided (not shown in FIG. 5) at the site of the respective battery cell 101-1-101-3.

It is possible that the control entity 510 is configured to monitor one or more operation parameters, e.g., the operation parameter may comprise at least one parameter consisting of: pressure of the respective battery cell 101-1-101-3; temperature of the respective battery cell 101-1-101-3; color of an electrode of the at least one battery cell 101-1-101-3; dilatation of the at least one battery cell 101-1-101-3; voltage across the at least one battery cell 101-1-101-3; and voltage across the battery 102. Alternatively or additionally, the control entity 510 can be configured to monitor the overall voltage across the entire battery 102. Other operation parameters are conceivable. Such operation parameters as mentioned above, may be suited to determine the SOC and/or SOH of the battery 102. Typically, it may be possible to determine a concentration of certain materials, e.g., Lithium, from the color of the electrode.

Monitoring the operation parameter may refer to: in response to a control command, sensing the operation parameter; and/or at predefined repetition times, sensing the operation parameter.

As battery cells 101-1-101-3, Lithium Ion cells, or any other kind of rechargeable cells may be used, such as, e.g., NiZnCells, NiMHcells, NiCdcells, Lead-acid cells, etc. E.g., each of the cells may provide a voltage of between e.g., 1V and 6 V, between 1V (or 2 V) and 4 V, or between 3 V and 4 V, etc.

As shown in FIG. 5, the monitoring device 110 further comprises an interface 520. The interface 520 is configured to transmit the control data via load modulation of a power line signal of the power line 180. The interface 520 is further configured to receive the control data via load demodulation of the power line signal. Thus, via the interface 520, bi-directional communication with the master unit 120 can be achieved. For this, as shown in FIG. 5, the interface 520 can manipulate a branch of the power line 180 electrically connected in parallel to the battery 102, i.e., electrically connected in parallel to the three battery cells 101-1-101-3 of the battery 102. In particular, a load associated with this branch of the power line 180 can be manipulated when employing techniques of load modulation and load demodulation.

Figure 6:
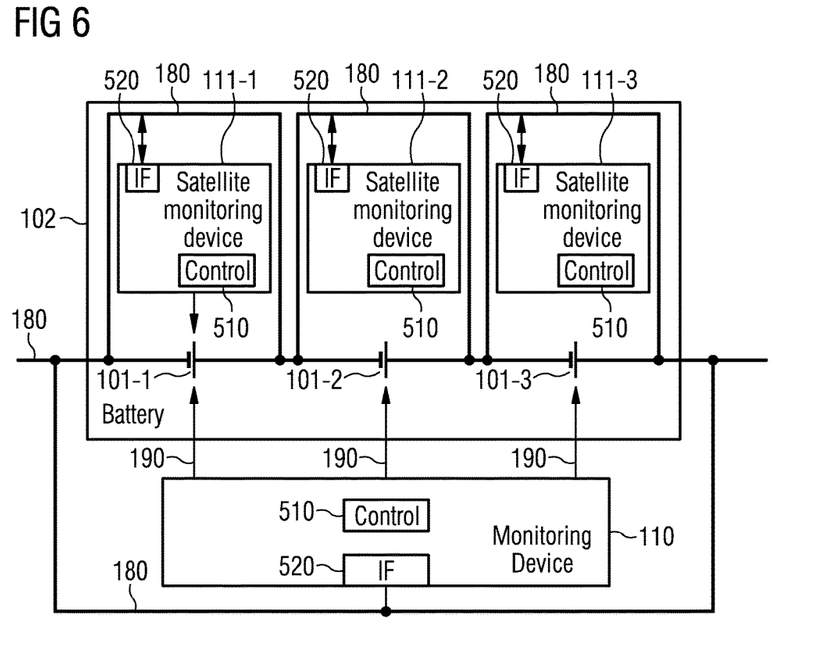
FIG. 6 illustrates a battery, satellite monitoring devices, and a monitoring device according to various embodiments.

In FIG. 6, a scenario is shown where each one of the battery cells 101-1-101-3 is associated with a satellite monitoring device 111-1-111-3. Each one of the satellite monitoring devices 111-1-111-3 comprises a control entity 510 which is configured to monitor the operation parameter of the associated battery cell 101-1-101-3. Further, each one of the satellite monitoring devices 111-1-111-3 comprises an interface 520 which is coupled with a respective branch of the power line 180 and configured to receive control data via load demodulation of the power line signal and further configured to transmit control data via load modulation of the power line signal. The monitoring device 110 and the satellite monitoring devices 111-1-111-3 may operate according to common techniques. The particular operation parameter monitored by one of the satellite monitoring devices 111-1-111-3 versus the monitoring device 110 may, however, differ. E.g., the monitoring device 110 can be configured to monitor the overall voltage across the battery 102; likewise, each one of the satellite monitoring devices 111-1-111-3 may be configured to monitor the pressure and temperature and dilatation of the respective battery cell 101-1-101-3.

In a simple scenario, both, the monitoring device 110 as well as the satellite monitoring device 111-1-111-3 are configured to transmit control data via load modulation to the master unit 120. E.g., the satellite monitoring device 111-1-111-3 can be configured to transmit the control data directly to the master unit 120. However, it would also be possible that the monitoring device 110 acts as a transponder for the control data transmitted by the satellite monitoring devices 111-1-111-3 and transmitted by the master unit 120 to the satellite monitoring devices 111-1-111-3.

Figure 7:
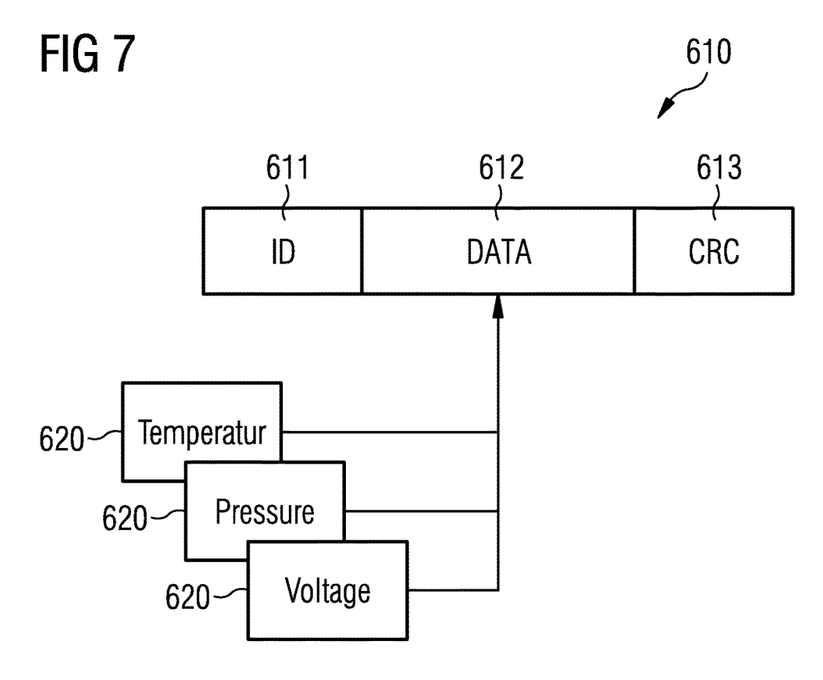
FIG. 7 illustrates packetized control data.

In FIG. 7, details of the control data 610 are shown. The control data can be packetized data which comprises a header 611, a payload section 612, and a checksum 613. The checksum 613 may be used to reduce a likelihood of transmission errors. The payload section 612 carries variable information relating to, e.g., the operation parameter 620 or a command addressed to one of the monitoring devices 110 or to one of the satellite monitoring devices 111, 111-1-111-

3. In the scenario of FIG. 7, information on three operating parameters 620 relating to the temperature, the pressure, and the voltage drop across a certain battery cell 101-1-101-12 is included in the payload section 612. As mentioned above, various information can be included in the payload section 612. E.g., the control data 610 can be indicative by at least element selected from the group consisting of: an identification of the at least one battery cell 101-1-101-12 or battery 102; an identification of the monitoring device 110 and/or the satellite monitoring device 111, 111-1-111-3; the operation parameter 620; a control command for the control entity 510; and a communication setup parameter.

The identification can be associated with an originator or recipient of the particular control data 610; it can be also included in the header section 611. As can be seen from FIG. 7, by means of the identification, the packetized control data 610 can be selectively communicated between the master unit 120 and a respective monitoring device 110, 111-1-111-3 thus identified, i.e. point-to-point communication may be implemented. Also point-to-multipoint techniques may be applied.

Multiple packets of the control data 610 may be transmitted via the power line 180 in a time-multiplexed manner. Alternatively or additionally, it is also possible that the control data 610 is transmitted in a frequency-multiplexed manner. Here, different originators corresponding to the various monitoring devices 110, 111 or the master unit 120 may be configured to transmit the control data via different modulation channels, i.e., in different frequency bands. By such means, the data throughput may be increased.

Figure 8:
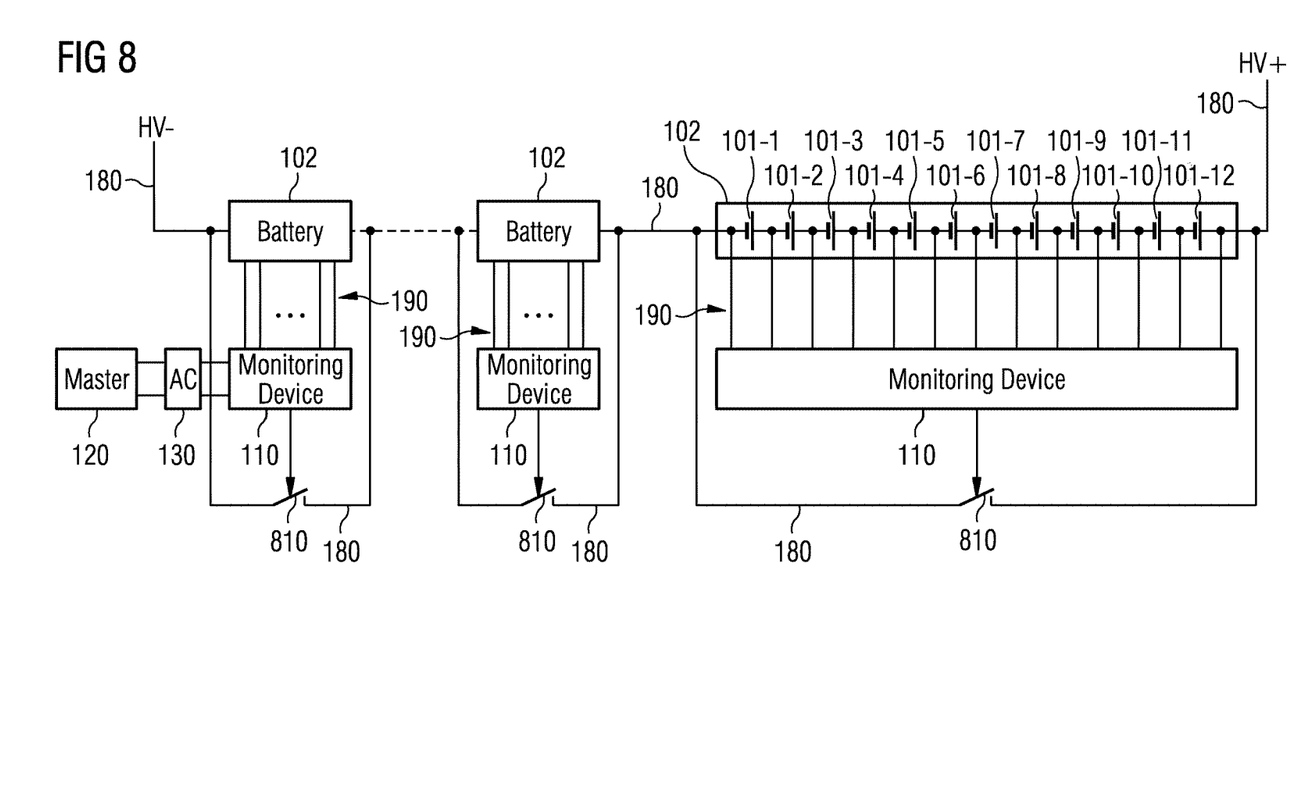
FIG. 8 illustrates a BMS according to various embodiments in greater detail.

Turning to FIG. 8, details of the load modulation and load demodulation of the power line signal are shown. In the scenario of FIG. 8, in the branches of the power line 180 running in parallel to the respective batteries 102, switches 810, e.g., in the form of load modulation transistors, are provided. The interfaces 520 (not shown in FIG. 8) of the monitoring devices 110 can control the switches 810. In particular, the interfaces 520 are configured to transmit the control data 620 via time-dependent variation of an impedance connected in parallel to the battery cells 101-1-101-12 associated with the respective monitoring device 110. By means of this time-dependent variation, the control data 620 is encoded. For this, the switches 810 may be switched on and off over the course of time.

Techniques are discussed in FIG. 8 with respect to the monitoring devices 110 on the battery level. The corresponding techniques can be readily applied with respect to the satellite monitoring devices 111, 111-1-111-3 on the battery-cell level (cf. FIG. 6).

Figure 9:
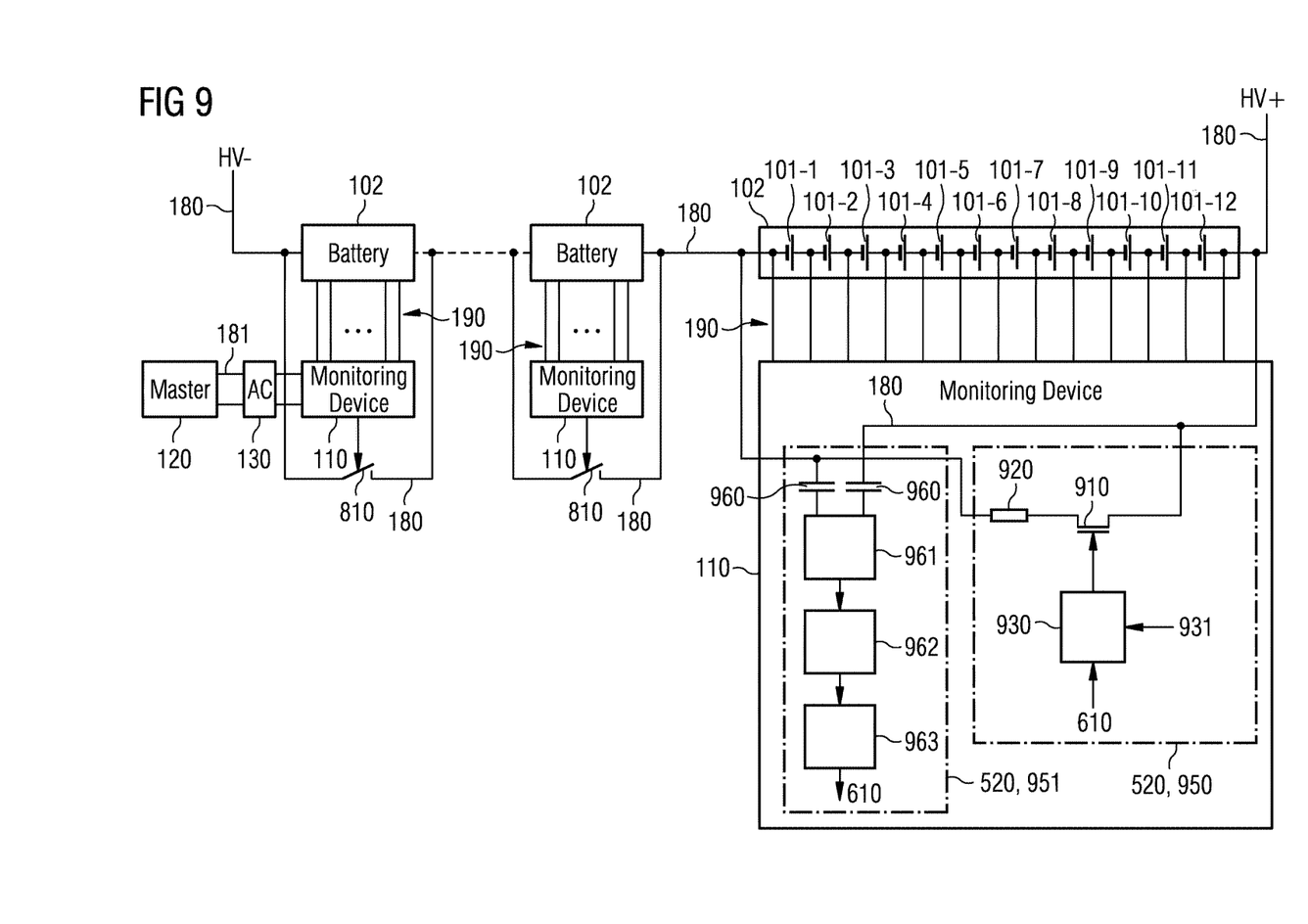
FIG. 9 illustrates a BMS according to various embodiments in greater detail.

In FIG. 9, the modulation and demodulation of the power line signal is shown at even greater detail. In particular, for one of the monitoring devices 110, a transmitter 950 and a receiver 951 of the interface 520 are shown. The transmitter (receiver) 950 is configured to transmit (receive) the control data 650 via load modulation (load demodulation) of the power line signal.

The transmitter 950 comprises a transistor 910 and a resistor 920. The resistor 920 and the transistor 910 are coupled in series in the branch of the power line 180 which, in turn, runs in parallel to the battery cells 101-1-101-12 of the associated battery 102. A modulator unit 930 switches the transistor 910 on and off over the course of line. As an input, the modulator unit 930 receives a predefined carrier signal 931 and the control data 610, e.g., digitally encoded as a bit sequence.

E.g., the modulator unit 930 may modulate the amplitude of the carrier signal 931 to further encode the control data.

It is also possible that the modulator unit 930 employs Phase Modulation (BPSK). BPSK modulation may increase the reliability against transmission errors. Further, a larger transmission capacity may be achieved by frequency multiplexing. For this purpose, different transmitters 950 of different monitoring devices 110 or satellite monitoring devices 111, 111-1-111-3 may modulate the control data 610 onto carrier signals 931 of different frequencies. In general, other modulation techniques may be employed, e.g., quadrature amplitude modulation (QAM) or frequency modulation (FM), or single-sideband modulation, etc.

It is possible to control the amplitude of the load modulation by respectively dimensioning the resistor 920 and/or the transistor 910. Generally, a larger amplitude of the load modulation will result in a larger signal-to-noise ratio of the modulated signal at the site of the master unit 120. Therefore, a larger amplitude may decrease the transmission error likelihood. On the other hand, it may be desirable to limit the modulation amplitude to a value allowing reliable transmission, thereby avoiding interference with other parts of the system and/or limiting power requirements.

The likelihood of transmission errors may be further influenced by a state of the batteries 102. In particular, the likelihood of transmission errors may be further influenced by the SOH and/or SOC of the batteries 102. Therefore, generally speaking, over the course of time the transmission reliability may degrade or improve. To counter such a time-dependency of the transmission reliability, it may be possible that the amplitude of the load modulation is dynamically set. E.g., the interface 520 can be configured to set an amplitude of the load modulation based on the operation parameter 620. The operation parameter 620, as mentioned above, may be indicative of the SOC and/or the SOH.

E.g., the setting of the amplitude of the load modulation may be part of a calibration routine. As part of the calibration routine, it could be possible to increment a resistance of the branch of the power line 180 incrementally, e.g., in steps corresponding to a change in current amounting to 100 mA. This can be achieved by connecting a plurality of the transistors 910 and/or the resistors 920 in parallel. At the same time, a signal-to-noise ratio of the control data transmitted via power line modulation and received by the master unit 120 can be determined. Once a predefined criterion for the signal-to-noise ratio is met, a respective setting for the amplitude of the load modulation can be adhered.

Above, the details of the transmitter 950 configured for load modulation of the power line signal are discussed. The transmitter 950 is different to transmitters conventionally employed for power line transmission. Conventional transmitters 950 typically comprise a power amplifier which adds additional power to the power line signal. In contrast, the present transmitter 950 generates a compensation current, i.e., effectively reduces the power of the power line signal. Such techniques of power line modulation were found to provide an increased signal-to-noise ratio and transmission reliability.

The receiver 951 comprises two capacitors 960, a band pass filter 961, an amplifier 962, and a demodulator unit 963. The control data 610 is output from the receiver 951, e.g., encoded as binary data.

It is possible that the satellite monitoring devices 111, 111-1-111-3 comprise transmitters 950 and receiver 951 corresponding to those discussed with respect to FIG. 9. Likewise, it is possible that the master unit 120 comprises a transmitter 950 and receiver 951 corresponding to those discussed with respect to FIG. 9. In particular, the master unit 120 may be directly coupled to the power line 180; however, in the scenario of FIG. 9, the master unit 120 is AC-coupled via dedicated control signal wiring 190 with one of the monitoring devices 110; the latter serves as a transponder for control data 610 sent to and from the master unit 120. AC-coupling allows AC transmission of signal, albeit a DC voltage difference may be present.

In a BMS 900, as shown in FIG. 9, the data traffic occurring at the various monitoring devices 110 is balanced. In particular, if compared to a conventional BMS 100 (see FIG. 1), spatially dependent heating of the BMS 900 can be avoided. Further, as various monitoring device 110 can employ different modulation channels, the transmission capacity of the BMS 900 can be increased if compared to conventional BMS 100 (see FIG. 1).

Figure 10:
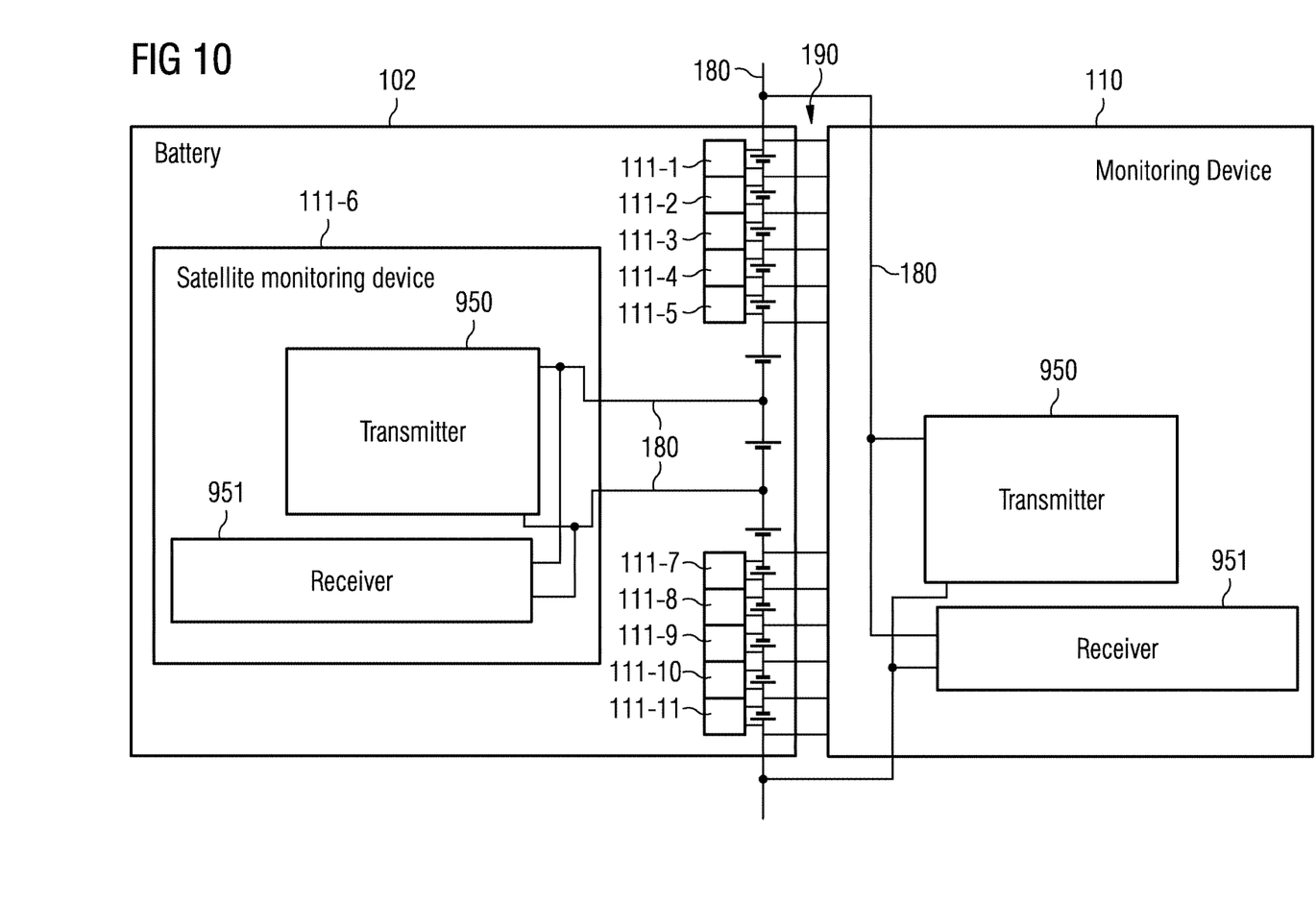
FIG. 10 illustrates a satellite monitoring device and a monitoring device of a BMS according to various embodiments.

In FIG. 9, details of the transmitter 950 and the receiver 951 are discussed on battery level, i.e., with respect to the monitoring devices 110 associated with a battery. However, similar techniques may be alternatively or additionally applied for satellite monitoring devices 111-1-111-11 on battery-cell level, as shown in FIG. 10. In FIG. 10, details of the satellite monitoring device 111-6 are shown for illustrative purposes—however, the remaining satellite monitoring devices 111-1-111-5, 111-7-111-11 can be configured correspondingly.

As mentioned above, it is possible that the transmitter 950 and the receiver 951 of the satellite monitoring devices 111-1-111-11 communicate directly with the master unit 120 (not shown in FIG. 10). However, alternatively or additionally, it is also possible that the transmitter 950 and receiver 951 of the satellite monitoring devices 111-1-111-11 communicate with the monitoring device 110 of the respective battery 102. It is not necessary, that the power line signaling of a particular satellite monitoring device 111-1-111-11 generates a sufficient signal-to-noise ratio to decode the control data 610 in the entire circuit formed by the power line 180. Rather, it is sufficient if the satellite monitoring devices 111-1-111-11 generate a sufficient signal-to-noise ratio to decode the control data 610 in the battery-level circuit of the respective battery 102. By this, exchange of the control data between battery level and battery-cell level is facilitated.

Figure 11:
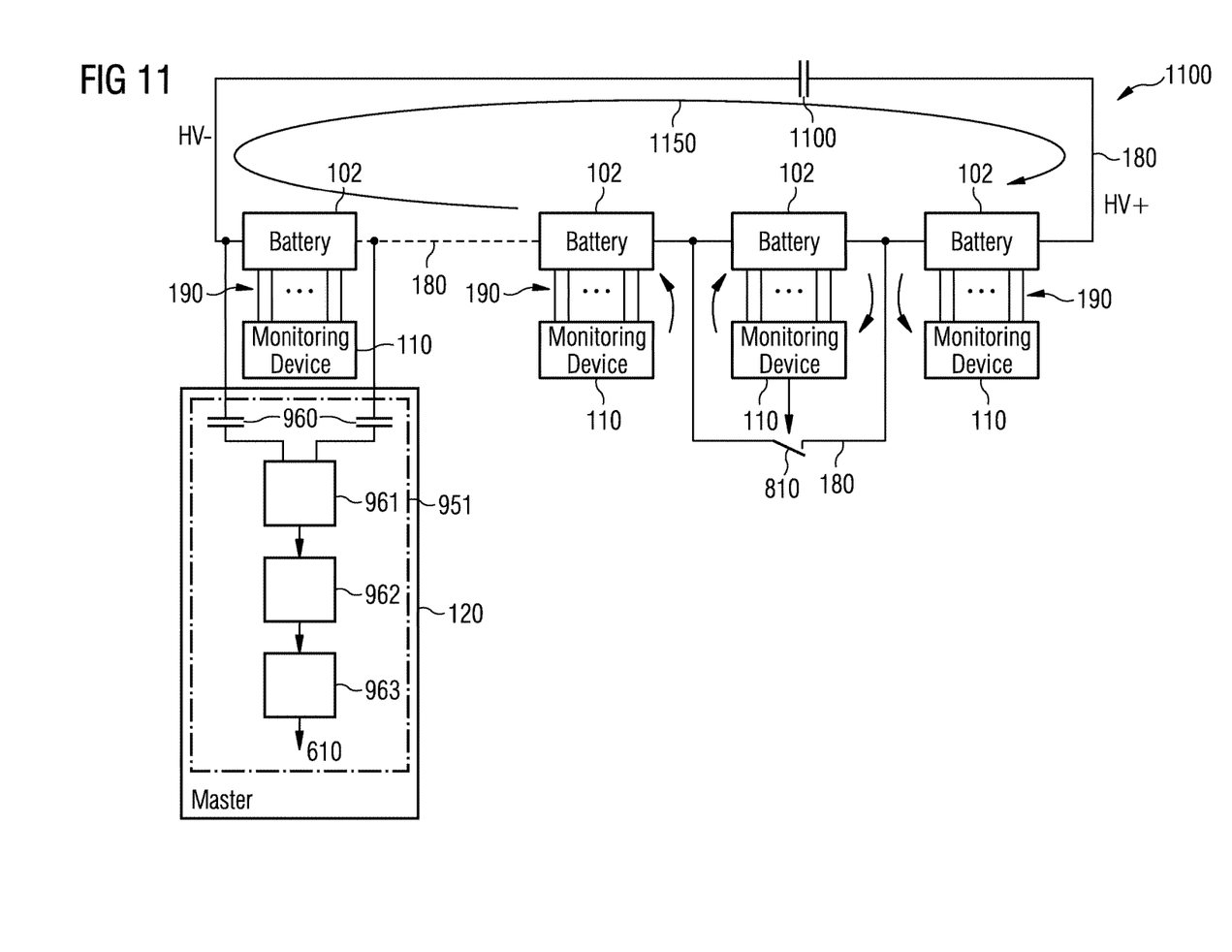
FIG. 11 illustrates a compensating current occurring when load modulating a power line signal according to various embodiments.

In FIG. 11, details of the power line signaling employing load modulation and load demodulation are shown with respect to the BMS 1100. As can be seen from FIG. 11, the master unit 120 can be coupled with the power line 180, e.g., with a branch thereof in parallel with one of the batteries 120. The master unit 120 can comprise a transmitter 950 (not shown in FIG. 11). The master unit 120 in the scenario of FIG. 11 comprises a receiver 951 for demodulation of the power line signal.

Further, the physical phenomena underlying the load modulation are explained in FIG. 11. The load modulation transistor 910 is employed to vary the impedance in the respective branch of the power line 180. This generates a compensation current 1150 in the power line 180. As can be seen, a capacitor 1100 is present in the closed circuit formed by the power line 180 which supports the compensation current 1150. In particular, as the compensation current 1150 is present in the entire circuit formed by the power line 180, it can be detected by the receiver 951 of the master unit 120. Thereby, the monitoring devices 110 can communicate with the master unit 120. As further illustrated in FIG. 11 by the curved arrows, fractions of the compensation current 1150 distribute in the closed circuits formed by each battery 102 and load modulation transistor 910.

Figure 12:
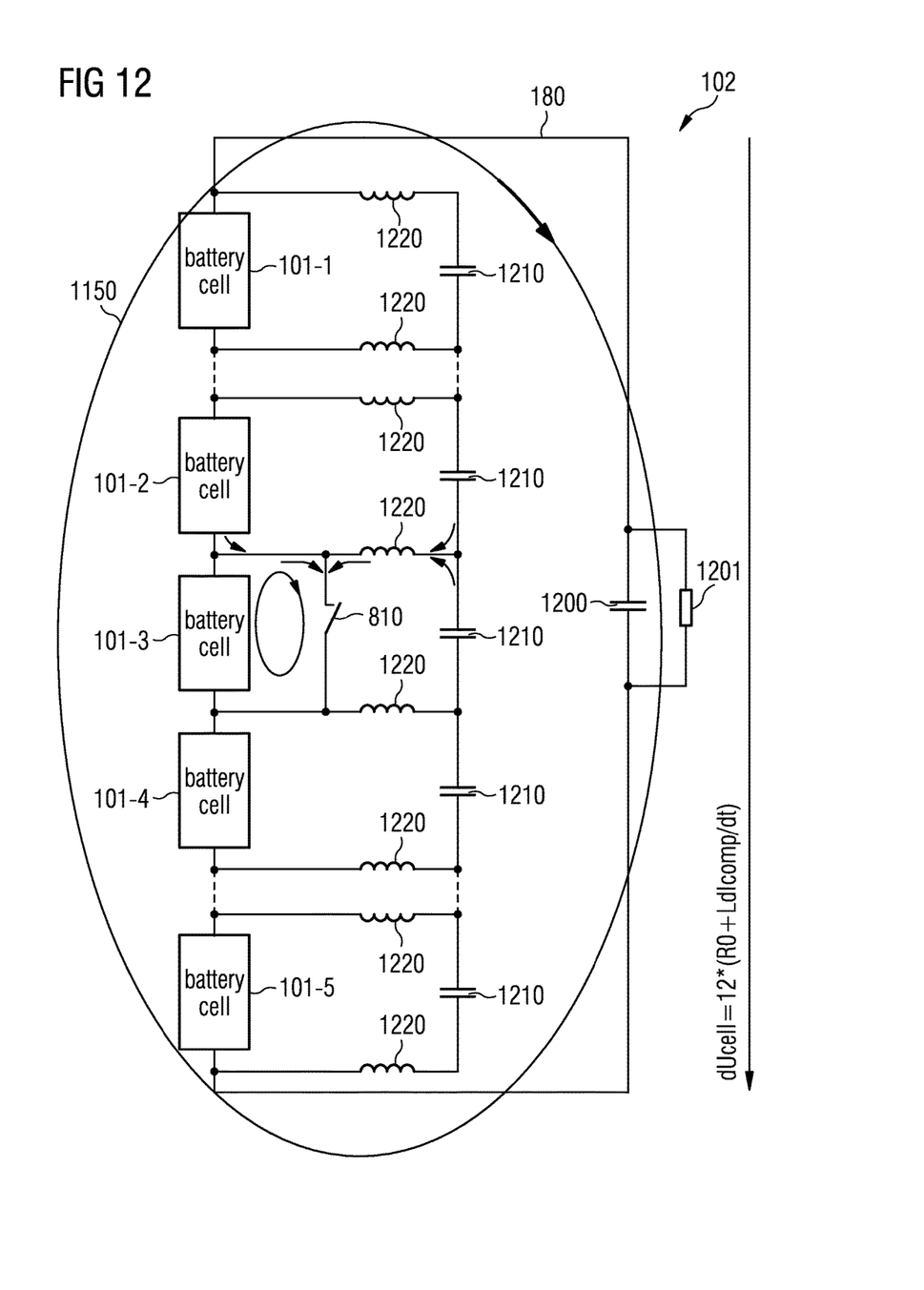
FIG. 12 illustrates a compensating current occurring when load modulation a power line signal in a battery of a BMS according to various embodiments.

In FIG. 12, the concept of load modulation and load demodulation of the power line signal is discussed on battery level. A similar concept can be employed for load modulation and load demodulation on battery-cell level, i.e., for the communication with satellite monitoring devices (not shown in FIG. 12). A number of battery cells 101-1-101-5 is depicted. Further shown in FIG. 12 are inductances 1220, so-called power inductances employed in the connection between battery cells 101-1-101-5 and the satellite monitoring devices. For the particular satellite monitoring device associated with battery cell 101-3, the load modulation transistor 810 is exemplarily shown. Modulation of the impedance in the respective branch of the power line 180 results in the compensation current 1150 across the entire battery-level circuit of the power line 180 of the respective battery 102. In particular, this compensation current 1150 is supported by a respective capacitor 1200 and a respective resistor 1201. As a result, the change of the impedance when operating the load modulation transistor 810 results in a change of the voltage drop across the entire battery 102. It is even possible that compensation currents from across the entire circuit of the BMS (cf. FIG. 11) are taken into account. This may be sensed by a respective monitoring device 110 (not shown in FIG. 12) and/or the master unit 120.

Figure 13:
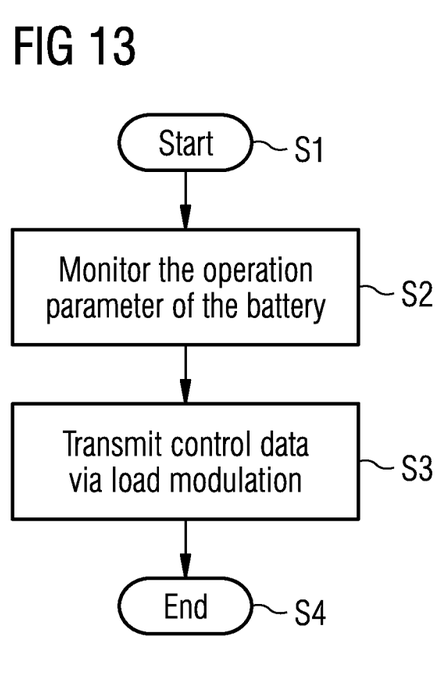
FIG. 13 is a flow chart of a method according to various embodiments.

In FIG. 13, a flow chart of a method according various embodiments is shown. At S1, the method starts. Next, at S2, the operation parameter 620 of the battery 102 is monitored. For this, the monitoring devices 110 on the battery level can be employed; additionally or alternatively, the satellite monitoring devices 111 on the battery-cell level can be employed. E.g., the operating parameter relating to the open circuit voltage across the battery 102 can be monitored by the monitoring device 110; while the operating parameters relating to temperature, dilatation, and pressure, can be monitored by the satellite monitoring devices 111.

Then, at S3, the control data 610 is transmitted via load modulation of the power line signal. The control data can, in particular, include the operation parameters of S2. The master unit 120 may receive the control data 610 via load demodulation of the power line signal.

The method ends at S4.

As already emphasized, the above-discussed embodiments serve only as examples, and various modifications and variations, some of which already have been described above, are possible without departing from the scope of the application.

Above, techniques of power line modulation in a BMS have been shown. In particular, load modulation and load demodulation is employed to modulate the power line signal. The load modulation results in formation of a compensation current which can be measured. More generally, a change in the impedance of the branch of the power line 180 in parallel to one of the batteries 102 results in a variation of the current at the master unit 120, respectively the voltage across a respective battery 102. This may be achieved by variation of the resistance in the branch of the power line 180, i.e., by ohmic load modulation. If compared to conventional techniques of power line modulation where additional signal power is applied on top of the power line signal, a more efficient and reliable transmission of the control data may be achieved.

The invention claimed is:
1. A device, comprising:
a control entity configured to monitor an operation parameter of a plurality of battery cells of a battery that is coupled along a power line between endpoints of the power line, the plurality of battery cells being electrically connected in series along the power line between terminals of the battery;
an interface configured to be coupled with the power line and to transmit control data on the power line via modulation of a power line signal by a switch connected in parallel with the plurality of battery cells and operating between an open state, in which a voltage according to a sum of open circuit voltages of the plurality of battery cells is developed between the endpoints of the power line and a closed state, in which the voltage according to the sum of open circuit voltages of the plurality of battery cells is not developed between the endpoints of the power line, wherein the modulation of the power line signal by the switch results in a compensation current that is detectable by a receiver; and
a capacitor configured to be coupled in parallel with the endpoints of the power line and to supplement the compensation current.

2. The device of claim 1,
wherein the control data is indicative of at least one element selected from the group consisting of:
an identification of the plurality of battery cells;
an identification of the battery;
an identification of the device;
the operation parameter;
a control command for the control entity; and
a communication setup parameter.

3. The device of claim 1,
wherein the operation parameter comprises at least one parameter consisting of:
a pressure of the plurality of battery cells;
a temperature of the plurality of battery cells;
a dilatation of the plurality of battery cells;
a color of an electrode of the plurality of battery cells;
a voltage across the plurality of battery cells; and
a voltage across the battery.

4. The device of claim 1,
wherein the interface is configured to set an amplitude of load modulation based on the operation parameter.

5. The device of claim 1, wherein the interface is configured to transceive or transmit and receive control data via the power line.

6. The device of claim 1,
wherein the interface is configured to transmit the control data via time-dependent variation of a transistor that corresponds to the switch, the time-dependent variation encoding the control data.

7. The device of claim 6,
wherein the interface comprises a resistor, the resistor being coupled in series with the transistor,
wherein both the transistor and the resistor are situated in a branch of the power line connected in parallel to the plurality of battery cells.

8. The device of claim 6,
wherein the interface is configured to modulate a predefined carrier signal to encode the control data,
wherein the time-dependent variation of the transistor corresponds to the modulated predefined carrier signal.

9. The device of claim 8,
wherein the interface is configured to modulate the carrier signal employing amplitude modulation or phase shift modulation.

10. A system, comprising:
a plurality of batteries coupled along a power line in series between endpoints of the power line;
a plurality of devices, each one of the plurality of devices being associated with a corresponding one of the plurality of batteries, each device comprising:
a control entity configured to monitor an operation parameter of the corresponding one of the plurality of batteries; and
an interface configured to be coupled with the power line and to transmit control data on the power line via modulation of a power line signal by a switch connected in parallel with the corresponding one of the plurality of batteries and operating between an open state, in which a voltage of the corresponding one of the plurality of batteries is developed between the endpoints of the power line, and a closed state, in which the voltage of the corresponding one of the plurality of batteries is not developed between the endpoints of the power line, wherein the modulation of the power line signal by the switch results in a compensation current that is detectable by a receiver, and
a capacitor coupled in parallel with the endpoints of the power line and configured to supplement the compensation current in the power line.

11. The system of claim 10,
wherein an interface of each one of a first device and a second device of the plurality of devices is configured to transmit control data via a particular modulation channel.

12. The system of claim 10, further comprising:
a master unit configured to control the plurality of devices and comprising an interface, the interface of the master unit being configured to receive the control data transmitted by each one of the plurality of devices via load demodulation of a power line signal and further being configured to transmit the control data to each one of the plurality of devices via load modulation of the power line signal.

13. The system of claim 12,
wherein the interface of the master unit is AC coupled to the power line or to a given one of the plurality of devices.

14. A system, comprising:
a plurality of battery cells of a battery coupled along a power line in series between endpoints of the power line;
a plurality of devices, each one of the plurality of devices being associated with a corresponding one of the plurality of battery cells, each device comprising:
a control entity configured to monitor an operation parameter of the corresponding one of the plurality of battery cells; and
an interface configured to be coupled with the power line and to transmit control data on the power line via modulation of a power line signal by a switch connected in parallel with the corresponding one of the plurality of battery cells and operating between an open state, in which a voltage of the corresponding one of the plurality of battery cells is developed between the endpoints of the power line, and a closed state, in which the voltage of the corresponding one of the plurality of battery cells is not developed between the endpoints of the power line, wherein the modulation of the power line signal by the switch results in a compensation current that is detectable by a receiver, and a capacitor coupled in parallel with the endpoints of the power line and configured to supplement the compensation current in the power line.

15. The system of claim 14, further comprising:
a transponder unit comprising an interface coupled with the power line and configured to transceive the control data to and from each one of the plurality of devices via at least one of load modulation and load demodulation of a power line signal; and
  a master unit configured to control the plurality of devices and comprising an interface, the interface of the master unit being configured to transceive the control data to and from the interface of the transponder unit.

16. The system of claim 15,
wherein the interface of the transponder unit and the interface of the master unit are configured to communicate via at least one of load modulation and load demodulation.

17. The system of claim 15,
wherein an interface of each one of a first device and a second device of the plurality of devices is configured to transmit the control data via a particular modulation channel.

18. A method, comprising:
monitoring an operation parameter of a plurality of battery cells of a battery that is coupled along a power line between endpoints of the power line, the plurality of battery cells being electrically connected in series along the power line between terminals of the battery; and
transmitting control data on the power line via modulation of a power line signal by a switch connected in parallel with the plurality of battery cells and operating between an open state, in which a voltage according to a sum of open circuit voltages of the plurality of battery cells is developed between the endpoints of the power line, and a closed state, in which the voltage according to the sum of open circuit voltages of the plurality of battery cells is not developed between the endpoints of the power line, wherein the modulation of the switch results in a compensation current that is detectable by a receiver, and wherein a capacitor coupled in parallel with the endpoints of the power line is configured to supplement the compensation current.

19. The method of claim 18,
wherein the transmitting further comprises:
encoding the control data by varying over time a state of the switch connected in parallel with the plurality of battery cells, wherein the state of the switch is the open state or the closed state.

20. The method of claim 19, further comprising:
modulating a predefined carrier signal to encode the control data,
wherein the time-dependent variation of the state of the switch corresponds to the modulated predefined carrier signal.

21. The method of claim 20,
wherein modulating the predefined carrier signal comprises amplitude modulation or phase shift modulation.

* * * * *